US008431392B2

(12) United States Patent
Seki

(10) Patent No.: US 8,431,392 B2
(45) Date of Patent: Apr. 30, 2013

(54) SHORTENED ALK1 REGULATORY FRAGMENT

(75) Inventor: Tsugio Seki, Martinez, GA (US)

(73) Assignee: Medical College of Georgia Research Institute, Inc., Augusta, GA (US)

( * ) Notice: Subject to any disclaimer, the term of this patent is extended or adjusted under 35 U.S.C. 154(b) by 164 days.

(21) Appl. No.: 12/790,144

(22) Filed: May 28, 2010

(65) Prior Publication Data

US 2011/0136894 A1 Jun. 9, 2011

Related U.S. Application Data

(63) Continuation of application No. PCT/US2009/069435, filed on Dec. 23, 2009.

(60) Provisional application No. 61/204,220, filed on Jan. 5, 2009.

(51) Int. Cl.
*C12N 15/00* (2006.01)
*C07H 21/02* (2006.01)
*C07H 21/04* (2006.01)

(52) U.S. Cl.
USPC ...... 435/320.1; 536/23.1; 536/23.5; 536/24.1

(58) Field of Classification Search .............. 435/320.1; 536/23.1, 23.5, 24.1
See application file for complete search history.

(56) References Cited

PUBLICATIONS

Birren et al., GenEmbl Accession No. AC161812, computer printout, pp. 16-22.*
Andreoli and Miller, "Anti-vascular endothelial growth factor therapy for ocular neovascular disease", Curr Opin Ophthalmol, 18:502-508 (2007).
Bodnar, et al., "Extension of life-span by introduction of telomerase into normal human cells", Science, 279:349-352 (1998).
Brandwijk, et al., "Targeted gene-delivery strategies for angiostatic cancer treatment", Trends Mol Med, 13:200-209 (2007).
Cowan, et al., "Targeting gene expression to endothelial cells in transgenic mice using the human intercellular adhesion molecule 2 promoter", Transplantation, 62:155-160 (1996).
Cowan, et al., "Targeting gene expression to endothelium in transgenic animals: a comparison of the human ICAM-2, PECAM-1 and endoglin promoters", Xenotransplantation, 10:223-231 (2003).
Finnefrock, et al., "PD-1 blockade in rhesus macaques: Impact on chronic infection and prophylactic vaccination", J of Immunology, 182:980-87 (2009).
Genbank Accession No. AC161812, Mus musculus chromosome 15, clone RP23-195124, 61 pages, submitted Jun. 22, 2005, first published Oct. 8, 2005, accessed Feb. 11, 2010.
Greenberger, et al., Transcription-controlled gene therapy against tumor angiogenesis J Clin Invest, 113:1017-1024 (2004).
Jones and Annex, "Growth factors for therapeutic angiogenesis in peripheral arterial disease", Curr Opin Cardiol, 22:458-463 (2007).
Kerbel, "Tumor angiogenesis", N Engl J Med, 358:2039-2049 (2008).
Khong, et al., "Angiogenesis as a therapeutic target in arthritis: learning the lessons of the colorectal cancer experience", Angiogenesis, 10:243-258 (2007).
Li, et al., "Shortened ALK1 regulatory fragment maintains a specific activity in arteries feeding ischemic tissues", Gene Therapy, 16:1034-41 (2009).
Molin and Post, "Therapeutic angiogenesis in the heart: protect and serve", Curr Opin Pharmacol, 7:158-163 (2007).
Nicklin, et al., "Analysis of cell-specific promoters for viral gene therapy targeted at the vascular endothelium", Hypertension, 38:65-70 (2001).
Ovcharenko, et al., "ECR Browser: a tool for visualizing and accessing data from comparisons of multiple vertebrate genomes", Nucleic Acids Res; 32:W280-286 (2004).
Savontaus, et al., "Transcriptional targeting of conditionally replicating adenovirus to dividing endothelial cells", Gene Ther, 9:972-979 (2002).
Seki, et al., "Arterial endothelium-specific activin receptor-like kinase 1 expression suggests its role in arterialization and vascular remodeling", Circ Res, 93:6852-689 (2003).
Seki, et al., "Isolation of a regulatory region of activin receptor-like kinase 1 gene sufficient for arterial endothelium-specific expression", Circ Res, 94:e72-77 (2004).
Thomas, et al., "Progress and problems with the use of viral vectors for gene therapy", Nat Rev Genet, 4:346-358 (2003).
Varda-Bloom, et al., "Tissue-specific gene therapy directed to tumor angiogenesis", Gene Ther, 8:819-827 (2001).

* cited by examiner

*Primary Examiner* — Shin-Lin Chen
(74) *Attorney, Agent, or Firm* — Pabst Patent Group LLP

(57) ABSTRACT

Regulatory elements for controlling expression of transgenes in angiogenic tissue are provided. One embodiment provides an isolated nucleic acid having at least 80%, 85%, 90%, 95%, 97%, 99% or 100% sequence identity to SEQ ID NO:1, or a fragment thereof that causes expression of a transgene in angiogenic tissue. Vectors containing SEQ ID NO:1 and one or more transgenes are also provided. A preferred vector is an adenovirus vector. The transgene can encode a cytotoxin, pro-apoptotic polypeptide, or a therapeutic polypeptide. SEQ ID NO:1 regulates the expression of the transgene such that the transgene is only expressed in angiogenic tissue including, but not limited to arteries feeding ischemic tissues. Methods of using vectors containing SEQ ID NO:1 are also provided.

8 Claims, 1 Drawing Sheet

SEQUENCE LISTING

```
<160> NUMBER OF SEQ ID NOS: 7

<210> SEQ ID NO 1
<211> LENGTH: 4858
<212> TYPE: DNA
<213> ORGANISM: Artificial Squence
<220> FEATURE:
<223> OTHER INFORMATION: Synthetic 4.8 kb Alk1 gene fragment

<400> SEQUENCE: 1
gaattctttg ggcctgtttc atttcgttct gtcctcagaa tataggaaca gctgggcctt      60
gtgagcaact aattcttgta gacttggacg cagtctgtaa ttccttttct atgtcctcat     120
tggcctgagg ccctagtgct ttctccaact cttgtcactc ctcccacatc cccgcccct     180 gccccaagct ccccgtgcac tatgggaggc ttgggttcac aagaacagcc caggcaccag    240
ccagtgtcgg aacgctaaga agaggggaaa gatgccaccc ctgtccacag cttctcttca    300
acctcctaaa ttgacttctc tccgtcttac ttcacaggcc tgcccacaga aactcttcag    360
tccccactga cccctcagc cacttccag ctcctgacct tacccatggt ccctatctg       420 cccttccca aggaggcgga ccttagactt gggctgcaga ggtcccatgg gtcctgtccc     480
actcaagaca gagagccgcc ggctggagaa tgaaaggctt accggaagcc atggcatgtg    540
ggaggaagag tgggtgtgaa gatggtcatg tatccaggct ccctgttcta tagagtgtaa    600
caaagcgacc accacaatct ggaaaagcag atactgtaat ccatagtact gcaagacatg    660
gtctgtcctg accctgaaat ttggttgagc cggggctctg gaaggtcatg gggctcacaa    720
ttcaagaagc tgctagcatg tggagctcag cagaggaagt aagaccagtg ggagcctccc    780
```

```
gcctttctct ccccagcct ctatccttgc caaaggatag ggcacctctg tcccatcttg      840
caaaatctac atgacaggca tgacacctta gagattgctt ctgtgttctc ccactgggct      900
agggccaccc cttccctagc cttctcaaat attagccgac aaactccttc cttgaggaac      960
ttagataggc accatcttt accgtttgaa agatggaaca ctatgctcat tagtagcggg     1020
gggggggggg gggttgaagc ccctggaggt gttagtgggg tcacagcaac tagcctggat     1080
tcccagctgg tggaactact tcaaggtccc ccacaaggat attcacaagg ctaagagtaa     1140
aactcaagtc ctgcccagga agcatagat tttcacccag tcccagcctg tactgccgat     1200
caggaagagg aagagtgtcc tgtcttcccc atcccgagcc ctctgcccaa ctccccagcc     1260
gcaggtccca gcctcacaag gttccatgcc ccaaattcta aagctcccca tctggtagtt     1320
gtgccccgcc cccatcccgt ggttgggggtc ccatcccggc tagacaaaaa ggacacggct     1380
gaacagaaaa gacaaggtgg ccttcctc tattctggcc acccctgacc tgagggagag     1440
gaacaactaa ctgtcaagcc ttgaggtgca cagaccagac tgactcagaa cggacctatc     1500
taggtttctt tagcccgagg ctgagcgttg atggccagca ctgtggacaa cggaagggaa     1560
caaaagtatt aagggtgaag ggctggaatt tggaggcaaa aagatttaag ccaactggag     1620
aatccaaagg gcggagccaa ctctggagca gacactccca gcccaaactc agctttctta     1680
gcgctgttcc ttaggagtga gcacaggtaa gttggctgct acctcacgcg ggtccctccc     1740
tgaagccctc acgaatctag atttctgcct ctgggtgcag gctaccctct cctggcctag     1800
agcgacgctt ccgcagctag ctcagtccct acgttcctac ccaggacgca cgggacccca     1860
atgcctgggt tcgaagcctg tcccttcgtg gcagggaggg gctggggtgg tcgcactcgg     1920
tctgcagccc tctagagccg agccctgctg ctgggaggcg tactgggcaa taggaaacga     1980
gttattagga gggagtggtg gagccgggcc aggcaggaag aagctagaat aagaaacatt     2040
ttgctccagc cccttcccag tccccggagg ccgccgcgcc agccgcgcag atcaagacct     2100
ttcccggccc cacaggccgg ctctggacgt gagaccccgg ccgcctccgg caaggagagg     2160
cgggggtcga gtcgccctgt ccaaaggtga gtcggagtgc cgctgggccg ggcagggrga     2220
cctgtccctg gtctcagggg gaccctttctt aaygtggatc tcaaagacct ctcagacggc     2280
gcgtggcagg gtcagtttta gccgggcaag acagtcagca gtcccctggt tgtggacaca     2340
cacctccctg ctaccccgac ctgagcgtgg aaggggggcgg gtcgagcacg gatgggaat      2400 caaaaaactt ttttttgctag gtatcctgag gcctttagct tctcttccct gccgagatta     2460
actcttctac ccttatctat aawggtaaaa cgggactgaa agattcttcc ctcctgagct     2520
ccagggtgct ctgttgacat aggagcgact tcccttgcgg aacctcctca tagagaccac     2580
ttaacctggc accccaatcc ttatctctat agggtcacag aattcgatga tcttcacttg     2640
gtattcccaa atctccggcc tccacagtgc tggatcacag gcatgcacta cttactgtac     2700
cccaacccag tatgtttctt gctcgtctca gacagactga atggaagcct ggaatggctg     2760
acagaccaag ggatctacct aactaaccca ctgcatgggg ttccaataca cagaaaggag     2820
gcaagttggg gaggtggaag cttgataata tgtcccagaa agatgtcttg ttgctaacta     2880
gctgactccc atctcaggta aagtctgcca ataatggctt cctgccccaa agccttggaa     2940
catgccctgt ctgcatttat ccacaaaagc ccttcggagt cctaactggc tactagctgg     3000
ggcaagaggc aggaggtcag gcagaagctg ggacacagct gcggcagtgc aggtctctat     3060
ttccttccct ggaccgggcc tctgggcaga ggaaacccag gcaggaaggc cagagcctcc     3120
actagaaagg ttcaccaaga ccctcagcct gaccctagac atcctgcccc caaaagcctc     3180
```

```
-continued
agcatcttgg gtcttcgttc agtaccaagc ttagagcacg ggcctctgtt gcataaccag    3240
tccttccagc ctaccggtgt cttctcacat gtgttggctc cctcactggg gatccagcct    3300
gcacactctg ccattcagaa agtctgtgtt cctgtttgac cccggtccct cttgctacag    3360
gctcagcact gtcttctggc tctgaggctt tgagaaggga agggtggtat agcttctgaa    3420
acgatagctg atttgggccc cgggttgagg gctatcacat cataccagaa tcacgactct    3480
taccagtgcc catcagactt ctggaagaac aaaaccctag caagagtga agcccaggca    3540 actctctgag gtcaaacact cggtgtctaa gtatgtttca cttcctgtac tactggccct    3600
ccccccagcc ctttcccagg acaatgaaga gagagaaggg ggcccagatg ctttgaagg     3660 agaaacagac ctttttatacg atgtgctata agcctgggga tgcaggtagg gactgacccc    3720
acccgctcag gacacagaga agaaagacca gtttggggag atggagtcta gagagggtac    3780
agcattcact ctgtaaccct ggctgtcctg gaactcactc tgtagaccag gctggcctcg    3840
gactcagaaa tccgcctgcc tctgcctctc aagtgctggg attaaaggcg tgtaccacca    3900
ctgcccgtct ggggtctaga ctcttgtgtt agactcctgt tactaatgga atctgacaag    3960
cctcccctgg atgaggctta ctctctcctt taagaccaga gctgcagggg agggccacga    4020
agagatgata cagcaggtaa tgatgcttgc tacgtaagct gggtgacctg agttcgatct    4080
ccagcgccca cgtaaaggcg gaaggagaaa acagctgca cagaattatc tctgactttc       4140
acacttgtac cttagcacga agaccctac agacagaccc agtaataatg aatacattta     4200
aaacaacaaa acccccccaga gctgtgtaag gtacctacac agacgtcaca cagttgtctc    4260
tgctcctggt ggtccccttta aaccccgtcc tgcttccagc ctgccctgag ctccctgctg    4320
tgcgtgactt cagcctgttc tatccaggcc tcaatctaaa caatcttgat tcctgttgcc    4380
ggcctggcgg gaccctgaat ggcaggaagt aaggacaaga gcctgtttat gtttgaagca    4440
gccaggctgg gggtggggag tggggggcact gggaaacggt gggcaggggt ggaggctgga    4500
gcgatgggca aacggctgag gacaagagat gagctatgag agagtcgtcc ttcccactgt    4560
agctctgtct gtctgcaacc ctcccggcct attaccctct gaacagttgc agtgggcaca    4620
gagccccggt cctctctggc tctcttcatt taaacacagt tctccaccct ttaccccccaa    4680 cagatggttt ccatggggaa gtgaaccagg acttcccttg caggccccgc cctaaagtca    4740
gacgtaggag ttgggaggtg gcttccctgc ctcccccac ccccaaaaa aaaccctcaca    4800 gtgatttcct ctggtaggag gagaccttgg tcaccacagc tatcacgttt tgcagatc     4858
```

<210> SEQ ID NO 2
<211> LENGTH: 5
<212> TYPE: PRT
<213> ORGANISM: Artificial Sequence
<220> FEATURE:
<223> OTHER INFORMATION: Synthetic conserved region of ICE-Like caspaces

<400> SEQUENCE: 2

Gln Ala Cys Lys Gly
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic polylinker

<400> SEQUENCE: 3

Gly Gly Gly Gly Ser

```
<210> SEQ ID NO 4
<211> LENGTH: 14
<212> TYPE: PRT
<213> ORGANISM: Artificial Sequence
<220> FEATURE:
<223> OTHER INFORMATION: Synthetic polylinker

<400> SEQUENCE: 4

Glu Gly Leu Ser Ser Gly Ser Gly Ser Glu Ser Leu Val Asp
1               5                   10

<210> SEQ ID NO 5
<211> LENGTH: 18
<212> TYPE: PRT
<213> ORGANISM: Artificial Sequence
<220> FEATURE:
<223> OTHER INFORMATION: Synthetic polylinker

<400> SEQUENCE: 5

Leu Glu Ser Gly Ser Val Ser Ser Glu Gln Leu Ala Gln Phe Arg Ser
1               5                   10                  15

Leu Arg

<210> SEQ ID NO 6
<211> LENGTH: 24
<212> TYPE: DNA
<213> ORGANISM: Artificial Sequence
<220> FEATURE:
<223> OTHER INFORMATION: Synthetic  forward primer in Alk1 intron 2
      sequence

<400> SEQUENCE: 6
agtgaaccag gacttccctt gcag                                          24

<210> SEQ ID NO 7
<211> LENGTH: 24
<212> TYPE: DNA
<213> ORGANISM: Artificial Sequence
<220> FEATURE:
<223> OTHER INFORMATION: Synthetic reverse primer in SD/SA sequence

<400> SEQUENCE: 7
cgggtacaat tccgcagctt ttag                                          24
```

SHORTENED ALK1 REGULATORY FRAGMENT

CROSS-REFERENCE TO RELATED APPLICATION

This application is a continuation of pending prior application No. PCT/US2009/069435 filed Dec. 23, 2009, entitled "Shortened Alk1 Regulatory Fragment", which claims benefit of and priority to U.S. Provisional Patent Application No. 61/204,220 filed on Jan. 5, 2009, and where permissible is incorporated by reference in its entirety.

FIELD OF THE INVENTION

The invention is generally related to gene regulatory elements and gene therapy, for example treatment of ischemic tissue and tumors.

BACKGROUND OF THE INVENTION

Targeted expression of therapeutic genes to the angiogenic vasculature would provide a valuable treatment option for a number of disorders, such as ischemic heart disease (Malin, D., et al., *Curr Opin Pharmacol*, 7:158-163 (2007)), diabetic retinopathy (Andreoli, C. M., et al., *Curr Opin Ophthalmol*, 18:502-508 (2007)), rheumatoid arthritis (Khong, T. L. et al., *Angiogenesis*, 10:243-258 (2007)), malignant tumors (Kerbel, R. S., *N Engl J Med*, 358:2039-2049 (2008)), and peripheral artery disease (Jones, W. S., et al., *Curr Opin Cardiol*, 22:458-463 (2007)). To date, a number of targeted gene-delivery strategies have been developed to express therapeutic genes in angiogenic vessels (Brandwijk, R. J., et al., *Trends Mol Med*, 13:200-209 (2007)). Focus has been placed on the improvement of delivery vehicles, both viral and non-viral, as well as on the isolation of endothelial cell (EC)-specific promoters from genes, such as vascular endothelial growth factor receptors (VEGF-R1 VEGF-R2) (Nicklin, S. A., et al., *Hypertension*, 38:65-70 (2001); Savontaus, M. J., et al., *Gene Ther*, 9:972-979 (2002)), intercellular adhesion molecule-2 (ICAM-2) (Nicklin, S. A., *Hypertension*, 38:65-70 (2001)), von Willebrand factor (Nicklin, S. A., et al., *Hypertension*, 38:65-70 (2001)), and preproendothelin 1 (PPE) (Varda-Bloom, N., *Gene Ther*, 8:819-827 (2001); Greenberger, S., *J Clin Invest*, 113:1017-1024 (2004)). However, except for the PPE promoter, these promoters are not specific for angiogenic blood vessels. Unlike these pan-EC promoters, the mouse activin receptor-like kinase 1 (Alk1; Acvrl1) promoter induces transgene expression specifically in ECs of newly forming and remodeling arteries that feed ischemic lesions and developing tumors.

ALK1 is one of the type I receptors for the transforming growth factor β (TGF-β) superfamily ligands. Using Alk1$^{+/lacZ}$ reporter knock-in mice it was established that Alk1 gene expression is detected in a transient manner in the arteries feeding ischemic tissues (Seki, T., et al., *Circ Res*, 93:682-689 (2003)). The Alk1 gene regulatory region was isolated as a 9.2 kb Alk1 regulatory fragment (Seki, T., et al., *Circ Res*, 94:e72-77 (2004)). The transgenic mouse line with this 9.2 kb fragment, Tg(Alk1-lacZ), virtually recapitulated the reporter gene expression pattern observed in Alk1$^{+/lacZ}$ mice. The viral gene transfer vectors used in gene therapy, however, have limited payload capacities, and the 9.2 kb fragment is too large to be utilized in most of the vectors (Thomas, C. E., et al., *Nat Rev Genet*, 4:346-358 (2003)).

Therefore, it is an object of the invention to provide nucleic acid constructs that targets expression of therapeutic genes to the angiogenic vasculature.

It is another object of the invention to provide compositions and methods for treating ischemic heart disease, diabetic retinopathy, rheumatoid arthritis, malignant tumors, and peripheral artery disease.

It is an object of the invention to provide an isolated nucleic acid containing regulatory elements sufficient to target gene expression to the angiogenic vasculature.

It is yet another object to provide a transgenic host containing a nucleic acid construct that targets expression of therapeutic genes to the angiogenic vasculature.

SUMMARY

Regulatory elements for controlling expression of transgenes in angiogenic vascular tissue are provided. One embodiment provides an isolated nucleic acid having at least 80, 85, 90, 95, 97, 99 or 100% sequence identity to SEQ ID NO:1, or a fragment thereof that functions as a regulatory element to cause transcription of an associated transgene in angiogenic vascular cells or tissues. Vectors containing SEQ ID NO:1 and one or more transgenes are also provided. A preferred vector is an adenovirus vector. The transgene can encode a cytotoxin, pro-apoptotic polypeptide, or a therapeutic polypeptide. SEQ ID NO:1 regulates the expression of the transgene such that the transgene is only expressed in angiogenic tissue including, but not limited to arterial endothelial cells and arteries feeding ischemic tissues.

Methods of using vectors containing SEQ ID NO:1 are also provided. One method includes administering a vector containing a transgene under the control of SEQ ID NO:1 to angiogenic tissue of a tumor. In this embodiment, the transgene encodes a cytotoxin or a pro-apoptotic polypeptide, and when the cytotoxin or pro-apoptotic polypeptide is expressed in the angiogenic tissue, the angiogenic tissue is killed. Additionally, the cytotoxin or pro-apoptotic polypeptide can be released or secreted from the angiogenic tissue in an amount effective to kill nearby tumor tissue.

When the transgene encodes a therapeutic polypeptide the vector can be administered to a subject in need thereof to assist in regenerating ischemic tissue or damaged tissue. For example, the transgene can encode a growth factor that is released or secreted to surrounding tissue. The growth factor can help heal damaged tissue by triggering signal transduction in surrounding tissue to repair damaged tissue. In certain embodiments new blood vessels are induced to form.

The vectors can also be used to treat diabetic retinopathy, rheumatoid arthritis, and peripheral artery disease by administering the vector to a subject in need thereof wherein the vector expresses a transgene in an amount effective to alleviate one or more symptoms of diabetic retinopathy, rheumatoid arthritis, and peripheral artery disease.

DETAILED DESCRIPTION OF THE INVENTION

I. Definitions

Figure 1:
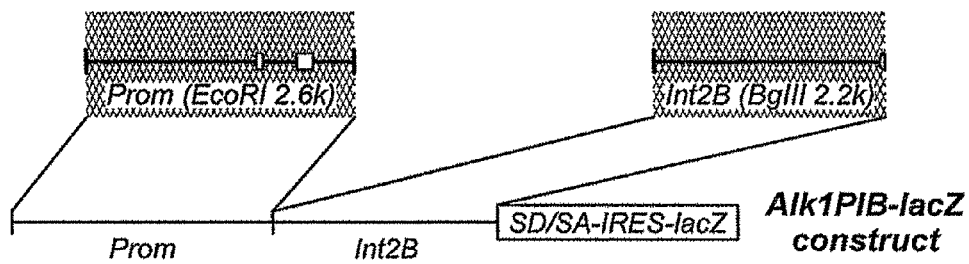
FIG. 1 is a schematic diagram of construct Alk1 PIB-lacZ.

The term "angiogenesis" refers to a myriad of different cellular events that occur after vasculogenesis that lead to the development of new blood vessels through sprouting from pre-existing vessels. This process involves the migration and proliferation of endothelial cells from pre-existing vessels. Angiogenesis is not limited to the embryonic period of development but also occurs in adults where the formation of vessels is required and is of particular significance in wound healing, ischemia, and tumor development.

The term "isolated" is meant to describe a compound of interest (e.g., a polynucleotide) that is in an environment different from that in which the compound naturally occurs e.g. separated from its natural milieu such as by concentrating a peptide to a concentration at which it is not found in nature. "Isolated" is meant to include compounds that are within samples that are substantially enriched for the compound of interest and/or in which the compound of interest is partially or substantially purified.

The term "stringent conditions" refers to those hybridizing conditions that (1) employ low ionic strength and high temperature for washing, for example, 0.015M NaCl/0.0015M sodium citrate/0.1% SDS at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75M NaCl, 0.075M Sodium pyrophosphate, 5×Denhardt's solution, sonicated salmon sperm. DNA (50 g/ml), 0.1% SDS, and 10% dextran sulfate at 42° C., with washes at 42° C. in 0.2×SSC and 0.1% SDS. Altered DNA sequences which may be used in accordance with the invention include deletions, additions or substitutions of different nucleotide residues resulting in a sequence that encodes the same or a functionally equivalent gene product.

The term "suitable for internal administration" refers to those compounds suitable to be administered within the tissue of an organism, for example within a muscle or within a joint space, intradermally, subcutaneously or intravenously.

The term "nucleic acid" refers to both RNA and DNA including: cDNA, genomic DNA, plasmid DNA, condensed nucleic acid, or nucleic acid formulated with compounds able to prolong the localized bioavailability of a nucleic acid. In a preferred embodiment, the nucleic acid administered is plasmid DNA.

The term "vector" refers to a molecule incorporating nucleic acid sequences encoding a polypeptide as well as, various regulatory elements for transcription, translation, transcript stability, replication, and other functions as are known in the art. A vector may be a nucleic acid such as a plasmid or other DNA vector. Alternatively, a vector may be modified virus whose native form contains the genomic material of a viral particle. The term "transcript stabilizer" is a sequence within the vector which contributes to prolonging the half life (slowing the elimination) of a transcript. The term "post-translational processing" means modifications made to the expressed gene product. These may include addition of side chains such as carbohydrates, lipids, inorganic or organic compounds, the cleavage of targeting signals or propeptide elements, as well as the positioning of the gene product in a particular compartment of the cell such as the mitochondria, nucleus, or membranes. The vector may comprise one or more genes in a linear or circularized configuration. The vector may also have a plasmid backbone or other elements involved in the production, manufacture, or analysis of a gene product. An "expression vector" is a vector that allows for production of a product encoded for by a nucleic acid sequence contained in the vector. For example, expression of a particular growth factor protein encoded by a particular gene. A "gene product" means products encoded by the nucleic acid sequences of the vector.

The terms "promoter" and "regulatory sequence" refer to a DNA sequence that controls and regulates the transcription of another DNA sequence.

The term "operably linked" means incorporated into a vector so that regulatory sequences effectively control expression of a coding sequence of interest.

The term "host cell" refers to prokaryotic and eukaryotic cells into which an expression vector can be introduced.

The terms "transformed" and "transfected" encompass the introduction of a nucleic acid (e.g. a vector) into a cell by a number of techniques known in the art.

The phrase "prolong the localized bioavailability of a nucleic acid" refers to a nucleic acid when administered to an organism in a composition having such a compound will be available for uptake by cells for a longer period of time than if administered in a composition without such a compound. This increased availability of nucleic acid to cells could occur, for example, due to increased duration of contact between the composition containing the nucleic acid and a cell or due to protection of the nucleic acid from attack by nucleases. The compounds that prolong the localized bioavailability of a nucleic acid are suitable for internal administration.

The compounds which prolong the localized bioavailability of a nucleic acid may also achieve one or more of the following effects, due to their physical or chemical properties: (1) protect nucleic acid, for example plasmid DNA, from nucleases; (2) increase the area of contact between nucleic acid, such as plasmid DNA, through extracellular matrices and over cellular membranes, into which the nucleic acid is to be taken up; (3) concentrate nucleic acid, such as plasmid DNA, at cell surfaces due to water exclusion; (4) indirectly facilitate uptake of nucleic acid, such as plasmid DNA, by disrupting cellular membranes due to osmotic, hydrophobic or lytic effects. The following compounds may be suitable for use as compounds which prolong the localized bioavailability of a nucleic acid: poloxamers; poloxamines; polyglutamate; ethylene vinyl acetates; polyethylene glycols; dextrans; polyvinylpyrrolidones; polyvinylalcohols; propylene glycols; and polyvinylacetates. These substances may be prepared as solutions, suspensions, gels, emulsions or microemulsions. "Solutions" refers to water soluble polymers and/or surfactants in solution with nucleic acids.

The compounds which prolong the bioavailability of a nucleic acid may also interact or associate with the nucleic acid by intermolecular forces and/or valence bonds such as: Van der Waals forces, ion-dipole interactions, ion-induced dipole interactions, hydrogen bonds, or ionic bonds. These interactions may serve the following functions: (1) stereoselectively protect nucleic acids from nucleases by shielding; (2) facilitate the cellular uptake of nucleic acid by "piggyback endocytosis". To achieve the desired effects set forth it is desirable, but not necessary, that the compounds which prolong the bioavailability of a nucleic acid have amphipathic properties; that is, have both hydrophilic and hydrophobic regions. The hydrophilic region of the compounds may associate with the largely ionic and hydrophilic regions of the nucleic acid, while the hydrophobic region of the compounds may act to retard diffusion of nucleic acid and to protect nucleic acid from nucleases. Additionally, the hydrophobic region may specifically interact with cell membranes, possibly facilitating endocytosis of the compound and thereby nucleic acid associated with the compound. This process may increase the pericellular concentration of nucleic acid. Agents which may have amphipathic properties and are generally regarded as being pharmaceutically acceptable are the following: poloxamers; poloxamines; ethylene vinyl acetates; polyethylene glycols; polyvinylpyrrolidones; polyvinylalcohols; and polyvinylacetates. Also, copolymer systems such as polyethylene glycol-polylactic acid (PEG-PLA), polyethylene glycol-polyhydroxybutyrie acid (PEG-PHB), polyvinylpyrrolidone-polyvinylalcohol (PVP-PVA), and derivatized copolymers such as copolymers of N-vinyl purine (or pyrimidine) derivatives and N-vinylpyrrolidone.

The term "poloxamer" refers to any di- or tri-block copolymer composed of the hydrophobe propylene oxide (POP, polyoxypropylene has the formula $(C_3H_6O)_x$) and the hydrophile ethylene oxide (POE, polyoxyethylene has the formula $(C_2H_4O)_x$). Poloxamers are in the polyglycol chemical family.

The common chemical name for poloxamers is polyoxypropylene-polyoxyethylene block copolymer. The CAS number is 9003-11-6.

The term "effective amount" refers to the administration of that amount to an individual, either in a single dose or as part of a series, effective for treatment of one or more symptoms of a disease or disorder of for prophylaxis or one or more symptoms of a disease or disorder. This amount varies depending upon the health and physical condition of the individual to be treated, the taxonomic group of individual to be treated (e.g., human, nonhuman primate, primate, etc.), the treating doctor's assessment of the medical situation, and other relevant factors. It is expected that the amount will fall in a relatively broad range that can be determined through routine trials.

II. Regulatory Sequences for Targeting Expression in Angiogenic Tissue

Regulatory sequences for targeting expression of a specific gene or nucleic acid to angiogenic tissue are provided. One embodiment provides an isolated nucleic acid including:

```
                                                        (SEQ ID NO: 1)
            gaattctttg ggcctgtttc atttcgttct gtcctcagaa tataggaaca gctgggcctt    60
gtgagcaact aattcttgta gacttggacg cagtctgtaa ttccttttct atgtcctcat   120
tggcctgagg ccctagtgct ttctccaact cttgtcactc ctcccacatc ccccgcccct   180
gccccaagct ccccgtgcac tatgggaggc ttgggttcac aagaacagcc caggcaccag   240
ccagtgtcgg aacgctaaga agaggggaaa gatgccaccc ctgtccacag cttctcttca   300
acctcctaaa ttgacttctc tccgtcttac ttcacaggcc tgcccacaga aactcttcag   360
tccccactga cccctcagc cacttcccag ctcctgacct tacccatggt ccctatctg    420 cccttccca aggaggcgga ccttagactt gggctgcaga ggtcccatgg gtcctgtccc    480
actcaagaca gagagccgcc ggctggagaa tgaaaggctt accggaagcc atggcatgtg   540
ggaggaagag tgggtgtgaa gatggtcatg tatccaggct ccctgttcta tagagtgtaa   600
caaagcgacc accacaatct ggaaaagcag atactgtaat ccatagtact gcaagacatg   660
gtctgtcctg accctgaaat ttggttgagc cggggctctg gaaggtcatg gggctcacaa   720
ttcaagaagc tgctagcatg tggagctcag cagaggaagt aagaccagtg ggagcctccc   780
gcctttctct cccccagcct ctatccttgc caaaggatag ggcacctctg tcccatcttg   840
caaaatctac atgacaggca tgacaccta gagattgctt ctgtgttctc ccactgggct    900
agggccaccc cttccctagc cttctcaaat attagccgac aaactccttc cttgaggaac   960
ttagataggc accatctttt accgtttgaa agatggaaca ctatgctcat tagtagcggg  1020
gggggggggg gggttgaagc ccctggaggt gttagtgggg tcacagcaac tagcctggat  1080
tcccagctgg tggaactact tcaaggtccc ccacaaggat attcacaagg ctaagagtaa  1140
aactcaagtc ctgcccagga aagcatagat tttcacccag tcccagcctg tactgccgat  1200
caggaagagg aagagtgtcc tgtcttcccc atcccgagcc ctctgcccaa ctccccagcc  1260
gcaggtccca gcctcacaag gttccatgcc ccaaattcta aagctcccca tctggtagtt  1320
gtgccccgcc cccatcccgt ggttggggtc ccatcccggc tagacaaaaa ggacacggct  1380
gaacagaaaa gacaaggtgg cctttccctc tattctggcc accccctgacc tgagggagag  1440 gaacaactaa ctgtcaagcc ttgaggtgca cagaccagac tgactcagaa cggacctatc  1500
taggtttctt tagcccgagg ctgagcgttg atggccagca ctgtggacaa cggaagggaa  1560
caaaagtatt aagggtgaag ggctggaatt tggaggcaaa aagatttaag ccaactggag  1620
aatccaaagg gcggagccaa ctctggagca gacactccca gcccaaactc agctttctta  1680
```

-continued

```
gcggtgttcc ttaggagtga gcacaggtaa gttggctgct acctcacgcg ggtccctccc 1740
tgaagccctc acgaatctag atttctgcct ctgggtgcag gctaccctct cctggcctag 1800
agcgacgctt ccgcagctag ctcagtccct acgttcctac ccaggacgca cgggacccca 1860
atgcctgggt tcgaagcctg tcccttcgtg cagggaggg gctggggtgg tcgcactcgg 1920
tctgcagccc tctagagccg agccctgctg ctgggaggcg tactgggcaa taggaaacga 1980
gttattagga gggagtggtg gagccgggcc aggcaggaag aagctagaat aagaaacatt 2040
ttgctccagc cccttcccag tccccggagg ccgccgcgcc agccgcgcag atcaagacct 2100
ttcccggccc cacaggccgg ctctggacgt gagaccccgg ccgcctccgg caaggagagg 2160
cgggggtcga gtcgccctgt ccaaaggtga gtcggagtgc cgctgggccg gcagggrga 2220 cctgtccctg gtctcagggg gacccttctt aaygtggatc tcaaagacct ctcagacggc 2280
gcgtggcagg gtcagtttta gccgggcaag acagtcagca gtccctggt tgtggacaca 2340 cacctccctg ctaccccgac ctgagcgtgg aaggggcgg gtcgagcacg gatggggaat 2400
caaaaaactt ttttttgctag gtatcctgag gcctttagct tctcttccct gccgagatta 2460
actcttctac ccttatctat aawggtaaaa cgggactgaa agattcttcc ctcctgagct 2520
ccagggtgct ctgttgacat aggagcgact tcccttgcgg aacctcctca tagagaccac 2580
ttaacctggc accccaatcc ttatctctat agggtcacag aattcgatga tcttcacttg 2640
gtattcccaa atctccggcc tccacagtgc tggatcacag gcatgcacta cttactgtac 2700
cccaacccag tatgtttctt gctcgtctca gacagactga atggaagcct ggaatggctg 2760
acagaccaag ggatctacct aactaaccca ctgcatgggg ttccaataca cagaaaggag 2820
gcaagttggg gaggtggaag cttgataata tgtcccagaa agatgtcttg ttgctaacta 2880
gctgactccc atctcaggta aagtctgcca ataatggctt cctgccccaa agccttggaa 2940
catgccctgt ctgcatttat ccacaaaagc ccttcggagt cctaactggc tactagctgg 3000
ggcaagaggc aggaggtcag gcagaagctg gacacagctc gcggcagtgc aggtctctat 3060
ttccttccct ggaccgggcc tctgggcaga ggaaacccag gcaggaaggc cagagcctcc 3120
actagaaagg ttcaccaaga ccctcagcct gaccctagac atcctgcccc caaaagcctc 3180
agcatcttgg gtcttcgttc agtaccaagc ttagagcacg ggcctctgtt gcataaccag 3240
tccttccagc ctaccggtgt cttctcacat gtgttggctc cctcactggg gatccagcct 3300
gcacactctg ccattcagaa agtctgtgtt cctgtttgac cccggtccct cttgctacag 3360
gctcagcact gtcttctggc tctgaggctt tgagaaggga agggtggtat agcttctgaa 3420
acgatagctg atttgggccc cgggttgagg gctatcacat cataccagaa tcacgactct 3480
taccagtgcc catcagactt ctggaagaac aaaaccctag gcaagagtga agcccaggca 3540
actctctgag gtcaaacact cggtgtctaa gtatgtttca cttcctgtac tactggccct 3600 cccccccagcc ctttcccagg acaatgagaa gagagaaggg ggcccagatg gctttgaagg 3660
agaaacagac cttttatacg atgtgctata agcctgggga tgcaggtagg gactgacccc 3720
acccgctcag gacacagaga agaaagacca gtttggggag atggagtcta gagagggtac 3780
agcattcact ctgtaaccct ggctgtcctg gaactcactc tgtagaccag gctggcctcg 3840
gactcagaaa tccgcctgcc tctgcctctc aagtgctggg attaaaggcg tgtaccacca 3900
ctgcccgtct ggggtctaga ctcttgtgtt agactcctgt tactaatgga atctgacaag 3960
cctcccctgg atgaggctta ctctctcctt taagaccaga gctgcagggg agggccacga 4020
agagatgata cagcaggtaa tgatgcttgc tacgtaagct gggtgacctg agttcgatct 4080
```

```
                                    -continued
ccagcgccca cgtaaaggcg gaaggagaaa aacagctgca cagaattatc tctgactttc 4140
acacttgtac cttagcacga agacccttac agacagaccc agtaataatg aatacattta 4200
aaacaacaaa accccccaga gctgtgtaag gtacctacac agacgtcaca cagttgtctc 4260
tgctcctggt ggtcccttta aaccccgtcc tgcttccagc ctgccctgag ctccctgctg 4320
tgcgtgactt cagcctgttc tatccaggcc tcaatctaaa caatcttgat tcctgttgcc 4380
ggcctggcgg gaccctgaat ggcaggaagt aaggacaaga gcctgtttat gtttgaagca 4440
gccaggctgg gggtggggag tggggcact gggaaacggt gggcaggggt ggaggctgga 4500
gcgatgggca aacggctgag gacaagagat gagctatgag agagtcgtcc ttcccactgt 4560
agctctgtct gtctgcaacc ctcccggcct attaccctct gaacagttgc agtgggcaca 4620
gagccccggt cctctctggc tctcttcatt taaacacagt tctccaccct ttacccccaa 4680
cagatggttt ccatggggaa gtgaaccagg acttcccttg caggccccgc cctaaagtca 4740
gacgtaggag ttgggaggtg gcttccctgc ctccccccac ccccaaaaa aaacctcaca 4800 gtgatttcct ctggtaggag gagaccttgg tcaccacagc tatcacgttt tgcagatc   4858
or a complement thereof.
```

Still another embodiment provides an isolated nucleic acid sequence having at least 80, 85, 90, 95, 97, or 99% sequence identity to SEQ ID NO:1 and causes expression of a transgene to occur in angiogenic tissue. Methods of determining sequence identity are routine and known in the art.

Still another embodiment provides a fragment of SEQ ID NO:1 and causes expression of a transgene to occur in angiogenic tissue. As used herein, a fragment of SEQ ID NO:1 refers to any subset of the polynucleotide that is at least one nucleotide shorter than full length protein. Useful fragments are those that retain the ability to causes expression of a transgene to occur in angiogenic tissue. A fragment of SEQ ID NO:1 typically has at least 80 percent, 90 percent, 95 percent, 98 percent, 99 percent, 100 percent, or even more than 100 percent of the ability to causes expression of a transgene to occur in angiogenic tissue as compared to full-length SEQ ID NO:1.

SEQ ID NO:1 is a 4.8 kb Alk1 gene fragment referred to as Alk1PIB and causes the expression of transgenes in angiogenic tissue. The term angiogenic tissue refers to, but is not limited to, newly forming and remodeling arteries associated with wound healing, ischemia, and tumor lesions.

The AlkPIB fragment was made by taking the promoter region (Prom), which is a 2.6 kb EcoRI-EcoRI fragment covering 1.7 kb of the promoter, exon 1, intron 1, exon 2, and a part of intron 2, as well as the 3' region of intron 2 (Int2B), which is a 2.2 kb BglII-BglII fragment covering 2 kb of intron 2 and a part of exon 3 (0.2 kb) upstream of the translation start site from genomic DNA. The Prom and Int2B fragments were ligated to create the 4.8 kb Alk1PIB regulatory fragment.

III. Alk1PIB Vectors

Vectors including SEQ ID NO:1 as a regulatory sequence are also provided. The vectors can be expression vectors, plasmids, viral vectors, or any nucleic construct containing a transgene under the control of SEQ ID NO:1, or a variant and/or fragment thereof. Representative viruses include adenovirus, adeno-associated virus, retrovirus, and herpes simplex virus. A preferred virus is adenovirus vector.

A. Adenovirus Vectors

Another embodiment provides a recombinant adenovirus vector containing the Alk1 PM fragment that induces transgene expression in arterial ECs. The Alk1PIB fragment can drive transgene expression in arterial SMCs at all stages examined. This additional expression may be due to the loss of an SMC-specific silencer element located in the deleted regions. Alternatively, reduction in the distance between the Prom and Int2B regions may have caused difficulty in forming a loop structure between these two regions, which may have lead to SMC expression.

B. Transgenes

1. Angiogenic Factors

Representative angiogenic factors encoded by the transgene in the vector include, but are not limited to, developmental endothelial locus-1 (Del-1), acidic and basic fibroblast growth factors (aFGF and bFGF), vascular endothelial growth factor (VEGF), epidermal growth factor (EGF), transforming growth factor-alpha and -beta (TGF-alpha and TFG-beta), platelet-derived endothelial growth factor (PD-ECGF), platelet-derived growth factor (PDGF), tumor necrosis factor-alpha (TNF-alpha), hepatocyte growth factor (HGF), insulin like growth factor (IGF), erythropoietin, colony stimulating factor (CSF), macrophage-CSF (M-CSF), granulocyte/macrophage CSF (GM-CSF) and nitric oxide synthase (NOS). Preferably, the angiogenic protein contains a secretory signal sequence allowing for secretion of the protein. Del-1 and VEGF are preferred angiogenic proteins. The vector can have one or more transgenes encoding polypeptides, preferably angiogenic factors.

Additional proteins that participate in the angiogenic process and can be encoded by the vector include, but are not limited to interleukin-S, angiopoietin-1, follistatin, platelet cell adhesion molecule (PECAM-1), tissue factor (TF, also known as thromboplastin), other mediators including hypoxia induced factor-1 (HIF-1), and platelet-activating factor (PAF), and factors affecting the proteolytic balance, such as for example, the matrix metalloproteinases (MMPs), tissue plasminogen activator (tPA), urokinase-type plasminogen activator (uPA) and plasminogen activator inhibitor-1 (PAI-1).

Vascular endothelial growth factor, ("VEGF"), is a homodimeric heavily glycosylated protein of 46-48 kDa (24 kDa subunits) although glycosylation is not required for biological activity. The homodimeric subunits are linked by disulphide bonds. The human gene has a length of approximately 12 kb and contains eight exons. At least four species of mRNA encoding VEGF-A have been identified and found to be expressed in a tissue-specific manner. The 165 amino acid form of the factor (VEGF-165) is the most common form found in most tissues. VEGF-121 and VEGF-165 are soluble secreted forms of the factor while VEGF-189 and VEGF-206 are mostly bound to heparin-containing proteoglycans on the cell surface or in the basement membrane. They arise from differential splicing with the 165 amino acid form of VEGF lacking sequences encoded by exon 6 and the 121 amino acid form lacking exon 6 and 7 sequences.

A high-affinity glycoprotein VEGF receptor of 170-235 kDa is expressed on vascular endothelial cells. The high-affinity receptor for VEGF, now known as VEGF-R1, has been identified as the gene product of the flt-1. Another receptor for VEGF, now known as VEGF-R2, is KDR, also known as flk-1. Signaling through the KDR/VEGFR-2 receptor up-regulates expression of integrin receptors.

Other VEGF-related factors are VEGF-B, which forms heterodimers with VEGF and VEGF-C (a.k.a. VEGF-2). VEGF-C is a protein of 23 kDa that is derived by proteolytic cleavage from a larger precursor. Another receptor for VEGF-C is Flt-4. VEGF-D has been described also and is the ligand for both KDR/Flk-1 and Flt-4. Thus, the ligands for KDR/VEGFR-2 include VEGF-A and VEGF-C and VEGF-D family members. In one embodiment, VEGF-A, C and D are used in conjunction to promote angiogenesis.

2. Cytotoxic Factors

Transgenes in the disclosed vectors can include genes that encode cytotoxic proteins or the vectors can include genes that encode enzymes that activate specific prodrugs. One embodiment provides a vector under the control of SEQ ID NO:1 wherein the transgene encodes a toxin that is released from the cell into the extracellular environment where it can kill neighboring cells, preferably tumor cells or vascular tissue supporting a tumor. Preferably, the toxin is derived or produced by bacteria or fungus. The transgene is expressed in arterial cells and toxin will be produced in these cells. The original toxin cDNA/gene may be of bacterial or fungal origin.

Another embodiment provides a vector that encodes proteins that promote apoptosis including, but not limited to cytochome c, apoptosis-inducing factor, caspace-2, granzyme B, perforin, granzymes, Bax, Bak, and proteins encoded by p53, p16, p21, p27, E2F, FHIT, PTEN and CASPASE 10.

The pro-apoptotic proteins in the BCL2 family are particularly suitable for use as the apoptosis-inducing moieties. These human proteins are expected to have reduced immunogenicity over many immunotoxins derived from bacterial toxins. Although Bax is a useful apoptosis-inducing moiety, other members in this family that can be used include Bak, Bcl-Xs, Bad, Bid, Bik, Hrk and Bok. The nucleotide sequences encoding these proteins are known in the art and are readily obtainable from databases such as GenBank, and thus cDNA clones can be readily obtained for fusion with a coding sequence for a cell-specific targeting moiety in an expression vector containing the regulatory sequence of SEQ ID NO:1.

Specific domains of particular members of the Bcl-2 family have been studied regarding their apoptosis-inducing activities. For example, the GD domain of Bak is involved in the apoptosis function (U.S. Pat. No. 5,656,725 to Chittenden et al.). In addition, Bax and Bipla share a homologous domain. Therefore, any biologically active domains of the Bcl-2 family may be used as an apoptosis-inducing moiety.

Caspases also play a central role in apoptosis and may well constitute part of the consensus core mechanism of apoptosis. Caspases are implicated as mediators of apoptosis. Since the recognition that CED-3, a protein required for developmental cell death, has sequence identity with the mammalian cysteine protease interleukin-1 beta-converting enzyme (ICE), a family of at least 10 related cysteine proteases has been identified. These proteins are characterized by almost absolute specificity for aspartic acid in the P1 position. All the caspases (ICE-like proteases) contain a conserved QACKG (where X is R, Z or G) pentapeptide active-site motif. Caspases are synthesized as inactive proenzymes comprising an N-terminal peptide (Prodomain) together with one large and one small subunit. The crystal structures of both caspase-1 and caspase-3 show that the active enzyme is a heterotetramer, containing two small and two large subunits. Activation of caspases during apoptosis results in the cleavage of critical cellular substrates, including poly (ADP-riose) polymerase and lamins, precipitating the dramatic morphological changes of apoptosis. Therefore, a caspase can be used as an apoptosis-inducing moiety.

In addition to cytochrome c the activation of caspase-3 requires two other cytosolic factors-Apaf-1 and Apaf-3. Apaf-1 is a protein homologous to *C. elegans* CED-4, and Apaf-3 was identified as a member of the caspase family, caspase-9. Both factors bind to each other via their respective $NH_2$-terminal CED-3 homologous domains, in the presence of cytochrome c, an event that leads to caspase-9 activation. Activated caspase-9 in turn cleaves and activates caspase-3. Another protein involved in the apoptotic pathway is DNA fragmentation factor (DFF), a heterodimer of 45 and 40 kd subunits that functions downstream of caspase-3 to trigger fragmentation of genomic DNA into nucleosomal segments.

3. Fusion Proteins

The transgene of the disclosed vectors can encode a fusion protein. Preferred fusion proteins include a cell-specific targeting moiety fused to an angiogenic factor, a cytotoxin, or a pro-apoptosis polypeptide. Fusion proteins are produced by fusing a coding sequence of a cell-specific targeting moiety and a coding sequence of an angiogenic factor or an apoptosis-inducing protein under the control of SEQ ID NO:1. In preferred embodiments, each of the components of the fusion protein has biologically functional activity as a cell-specific targeting moiety, angiogenic factor, or pro-apoptosis protein.

The fusion of two full-length coding sequences can be achieved by methods well known in the art of molecular biology. It is preferred that a fusion polynucleotide contain only the AUG translation initiation codon at the 5' end of the first coding sequence without the initiation codon of the second coding sequence to avoid the production of two separate encoded products. In addition, a leader sequence may be placed at the 5' end of the polynucleotide to target the expressed product to a specific site or compartment within a host cell to facilitate secretion or subsequent purification after gene expression. The two coding sequences can be fused directly without any linker or by using a flexible polylinker, such as the pentamer Gly-Gly-Gly-Gly-Ser (SEQ ID NO:2) repeated 1 to 3 times. The linker is designed to enable the correct interaction between two beta-sheets forming the variable region of the single chain antibody. Other linkers which may be used include Glu-Gly-Lys-Ser-Ser-Gly-Ser-Gly-Ser-Glu-Ser-Lys-Val-Asp (SEQ ID NO:3) and Lys-Glu-Ser-Gly Ser-Val-Ser-Ser-Glu-Gln Leu-Ala-Gln-Phe-Arg-Ser-Leu-Asp (SEQ ID NO:4).

a. Cell-Specific Targeting Moieties

The cell-specific targeting moiety confers cell-type specific binding to the fusion protein, and can be chosen on the basis of the particular cell population to be targeted. A wide variety of proteins are suitable for use as cell-specific targeting moieties, including but not limited to, ligands for receptors such as growth factors, hormones and cytokines, and antibodies or antigen-binding fragments thereof.

Certain cell surface molecules are highly expressed in tumor cells, including hormone receptors such as human chorionic gonadotropin receptor and gonadotropin releasing hormone receptor.

Tumor-Specific and Tumor-Associated Antigens

In one embodiment the fusion protein contains a domain that specifically binds to an antigen that is expressed by tumor cells. The antigen expressed by the tumor may be specific to the tumor, or may be expressed at a higher level on the tumor cells as compared to non-tumor cells. Antigenic markers such as serologically defined markers known as tumor associated antigens, which are either uniquely expressed by cancer cells or are present at markedly higher levels (e.g., elevated in a statistically significant manner) in subjects having a malignant condition relative to appropriate controls, are contemplated for use in certain embodiments.

Tumor-associated antigens may include, for example, cellular oncogene-encoded products or aberrantly expressed proto-oncogene-encoded products (e.g., products encoded by the neu, ras, trk, and kit genes), or mutated forms of growth factor receptor or receptor-like cell surface molecules (e.g., surface receptor encoded by the c-erb B gene). Other tumor-associated antigens include molecules that may be directly involved in transformation events, or molecules that may not be directly involved in oncogenic transformation events but are expressed by tumor cells (e.g., carcinoembryonic antigen, CA-125, melanoma associated antigens, etc.) (see, e.g., U.S. Pat. No. 6,699,475; Jager, et al., *Int. J. Cancer*, 106:817-20 (2003); Kennedy, et al., *Int. Rev. Immunol.*, 22:141-72 (2003); Scanlan, et al. *Cancer Immun.*, 4:1 (2004)).

Other tumor-associated antigens may or may not be directly involved in malignant transformation. These antigens, however, are expressed by certain tumor cells and may therefore provide effective targets. Some examples are carcinoembryonic antigen (CEA), CA 125 (associated with ovarian carcinoma), and melanoma specific antigens.

In ovarian and other carcinomas tumor associated antigens are detectable in samples of biological fluids such as serum or mucosal secretions. One such marker is CA125, a carcinoma associated antigen that is also shed into the bloodstream, where it is detectable in serum (Bast, et al., *N. Eng. J. Med*, 309:883 (1983); Lloyd, et al., *Int. J. Cana*, 71:842 (1997)). CA125 levels in serum and other biological fluids have been measured along with levels of other markers, for example, carcinoembryonic antigen (CEA), squamous cell carcinoma antigen (SCC), tissue polypeptide specific antigen (TPS), sialyl TN mucin (STN), and placental alkaline phosphatase (PLAP), in efforts to provide diagnostic and/or prognostic profiles of ovarian and other carcinomas (e.g., Sarandakou, et al., *Acta Oncol.*, 36:755 (1997); Sarandakou, et al., *Eur. J. Gynaecol. Oncol.*, 19:73 (1998); Meier, et al., *Anticancer Res.*, 17(4B):2945 (1997); Kudoh, et al., *Gynecol. Obstet. Invest.*, 47:52 (1999)). Elevated serum CA125 may also accompany neuroblastoma (e.g., Hirokawa, et al., *Surg. Today*, 28:349 (1998), while elevated CEA and SCC, among others, may accompany colorectal cancer (Gebauer, et al., *Anticancer Res.*, 17(4B):2939 (1997)).

The tumor associated antigen, mesothelin, defined by reactivity with monoclonal antibody K-1, is present on a majority of squamous cell carcinomas including epithelial ovarian, cervical, and esophageal tumors, and on mesotheliomas (Chang, et al., *Cancer Res.*, 52:181 (1992); Chang, et al., *Int. J. Cancer*, 50:373 (1992); Chang, et al., *Int. J. Cancer*, 51:548 (1992); Chang, et al., *Proc. Natl. Acad. Sci. USA*, 93:136 (1996); Chowdhury, et al., *Proc. Natl. Acad. Sci. USA*, 95:669 (1998)). Using MAb K-1, mesothelin is detectable only as a cell-associated tumor marker and has not been found in soluble form in serum from ovarian cancer patients, or in medium conditioned by OVCAR-3 cells (Chang, et al., *Int. J. Cancer*, 50:373 (1992)). Structurally related human mesothelin polypeptides, however, also include tumor-associated antigen polypeptides such as the distinct mesothelin related antigen (MRA) polypeptide, which is detectable as a naturally occurring soluble antigen in biological fluids from patients having malignancies (see WO 00/50900).

A tumor antigen may include a cell surface molecule. Tumor antigens of known structure and having a known or described function, include the following cell surface receptors: HER1 (GenBank Accession No. U48722), HER2 (Yoshino, et al., *J. Immunol.*, 152:2393 (1994); Disis, et al., *Canc. Res.*, 54:16 (1994); GenBank Acc. Nos. X03363 and M17730), HER3 (GenBank Acc. Nos. U29339 and M34309), HER4 (Plowman, et al., *Nature*, 366:473 (1993); GenBank Ace. Nos. L07868 and T64105), epidermal growth factor receptor (EGFR) (GenBank Acc. Nos. U48722, and KO3193), vascular endothelial cell growth factor (GenBank No. M32977), vascular endothelial cell growth factor receptor (GenBank Acc. Nos. AF022375, 1680143, U48801 and X62568), insulin-like growth factor-I (GenBank Acc. Nos. X00173, X56774, X56773, X06043, European Patent No. GB 2241703), insulin-like growth factor-II (GenBank Ace. Nos. X03562, X00910, M17863 and M17862), transferrin receptor (Trowbridge and Omary, *Proc. Nat. Acad USA*, 78:3039 (1981); GenBank Ace. Nos. X01060 and M11507), estrogen receptor (GenBank Acc. Nos. M38651, X03635, X99101, U47678 and M12674), progesterone receptor (GenBank Acc. Nos. X51730, X69068 and M15716), follicle stimulating hormone receptor (FSH-R) (GenBank Acc. Nos. Z34260 and M65085), retinoic acid receptor (GenBank Acc. Nos. L12060, M60909, X77664, X57280, X07282 and X06538), MUC-1 (Barnes, et al., *Proc. Nat. Acad. Sci. USA*, 86:7159 (1989); GenBank Acc. Nos. M65132 and M64928) NY-ESO-1 (GenBank Acc. Nos. AJ003149 and U87459), NA 17-A (PCT Publication No. WO 96/40039), Melan-A/MART-1 (Kawakami, et al., *Proc. Nat. Acad. Sci. USA*, 91:3515 (1994); GenBank Acc. Nos. U06654 and U06452), tyrosinase (Topalian, et al., *Proc. Nat. Acad. Sci. USA*, 91:9461 (1994); GenBank Ace. No. M26729; Weber, et al., *J. Clin. Invest*, 102:1258 (1998)), Gp-100 (Kawakami, et al., *Proc. Nat. Acad. Sci. USA*, 91:3515 (1994); GenBank Ace. No. 573003, Adema, et al., *J. Biol. Chem.*, 269:20126 (1994)), MAGE (van den Bruggen, et al., *Science*, 254:1643 (1991)); GenBank Acc. Nos. U93163, AF064589, U66083, D32077, D32076, D32075, U10694, U10693, U10691, U10690, U10689, U10688, U10687, U10686, U10685, L18877, U10340, U10339, L18920, U03735 and M77481), BAGE (GenBank Acc. No. U19180; U.S. Pat. Nos. 5,683,886 and 5,571,711), GAGE (GenBank Acc. Nos. AF055475, AF055474, AF055473, U19147, U19146, U19145, U19144, U19143 and U19142), any of the CTA class of receptors including in particular HOM-MEL-40 antigen encoded by the SSX2 gene (GenBank Acc. Nos. X86175, U90842, U90841 and X86174), careinoembryonic antigen (CEA, Gold and Freedman, *J. Exp. Med*, 121:439 (1985); GenBank Ace. Nos. M59710, M59255 and M29540), and PyLT (GenBank Acc. Nos. J02289 and J02038); p97 (melanotransferrin) (Brown, et al., *J. Immunol.*, 127:539-46 (1981); Rose, et al., *Proc. Natl. Acad Set. USA*, 83:1261-61 (1986)).

Additional tumor associated antigens include prostate surface antigen (PSA) (U.S. Pat. Nos. 6,677,157; 6,673,545);

n-human chorionic gonadotropin β-HCG) (McManus, et al., *Cancer Res.,* 36:3476-81 (1976); Yoshimura, et al., *Cancer,* 73:2745-52 (1994); Yamaguchi, et al., *Br. J. Cancer,* 60:382-84 (1989): Alfthan, et al., *Cancer Res.,* 52:4628-33 (1992)); glycosyltransferase β-1,4-N-acetylgalactosaminyltransferases (GalNAc) (Hoon, et al., *Int. J. Cancer,* 43:857-62 (1989); Ando, et al., *Int. J. Cancer,* 40:12-17 (1987); Tsuchida, et al., *J. Natl. Cancer,* 78:45-54 (1987); Tsuchida, et al., *J. Natl. Cancer,* 78:55-60 (1987)); NUC18 (Lehmann, et al., *Proc. Natl. Acad. Sci. USA,* 86:9891-95 (1989); Lehmann, et al., *Cancer Res.,* 47:841-45 (1987)); melanoma antigen gp75 (Vijayasardahi, et al., *J. Exp. Med.,* 171:1375-80 (1990); GenBank Accession No. X51455); human cytokeratin 8; high molecular weight melanoma antigen (Natali, et al., *Cancer,* 59:55-63 (1987); keratin 19 (Datta, et al., *J. Clin. Oncol.,* 12:475-82 (1994)).

Tumor antigens of interest include antigens regarded in the art as "cancer/testis" (CT) antigens that are immunogenic in subjects having a malignant condition (Scanlan, et al., *Cancer Immun.,* 4:1 (2004)). CT antigens include at least 19 different families of antigens that contain one or more members and that are capable of inducing an immune response, including but not limited to MAGEA (CT1); SAGE (CT2); MAGEB (CT3); GAGE (CT4); SSX (CT5); NY-ESO-1 (CT6); MAGEC(CT7); SYCP1 (CT8); SPANXBI (CT11.2); NA88 (CT18); CTAGE (CT21); SPA17 (CT22); OY-TES-1 (CT23); CAGE (CT26); HOM-TES-85 (C128); HCA661 (CT30); NY-SAR-35 (CT38); FATE (CT43); and TPTE (CT44).

Additional tumor antigens that can be targeted, including a tumor-associated or tumor-specific antigen, include, but not limited to, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAA0205, MaV2, Mum-1, 2, and 3, neo-PAP, myosin class I, OS-9, pml-RARα fusion protein, PTPRK, K-ras, N-ras, Triosephosphate isomeras, Bage-1, Gage 3,4,5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-1), gp100 (Pmel 17), tyrosinase, TRP-1, TRP-2, MAGE-1, MAGE-3, BAGS, GAGE-1, GAGE-2, p15 (58), CEA, RAGE, NY-ESO (LADE), SCP-1, Hom/Mel-40, PRAMS, p53, H-Ras, HER-2/neu, BCR-ABL, E2A-PRL, H4-RET, IGH-IGK, MYL-RAR, Epstein Barr virus antigens, EBNA, human papillomavirus (HPV) antigens 56 and 57, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGS, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (Ep-CAM), HTgp-175, M344, MA-50, MG7-Ag, MOV18, NB\70K, NY-CO-1, RCAS1, SDCCAG16, TA-90 (Mac-2 binding protein\cyclophilin C-associated protein), TAAL6, TAG72, TLP, and TPS. Other tumor-associated and tumor-specific antigens are known to those of skill in the art and are suitable for targeting by the disclosed fusion proteins.

In one embodiment, the tumor antigen is expressed on cancer stem cells. Exemplary cancer stem cell markers include but are not limited to CD133, CD40, CD44, and CD24.

Antigens Associated with Tumor Neovasculature

Protein therapeutics can be ineffective in treating tumors because they are inefficient at tumor penetration. Tumor-associated neovasculature provides a readily accessible route through which protein therapeutics can access the tumor. In another embodiment the fusion proteins contain a domain that specifically binds to an antigen that is expressed by neovasculature associated with a tumor.

The antigen may be specific to tumor neovasculature or may be expressed at a higher level in tumor neovasculature when compared to normal vasculature. Exemplary antigens that are over-expressed by tumor-associated neovasculature as compared to normal vasculature include, but are not limited to, VEGF/KDR, Tie2, vascular cell adhesion molecule (VCAM), endoglin and $\alpha_5\beta_3$ integrin/vitronectin. Other antigens that are over-expressed by tumor-associated neovasculature as compared to normal vasculature are known to those of skill in the art and are suitable for targeting by the disclosed fusion proteins b. Fc Domains In another embodiment, the targeting domains are Fc domains of immunoglobulin heavy chains that bind to Fc receptors. The Fc region a includes the polypeptides containing the constant region of an antibody excluding the first constant region immunoglobulin domain. Thus, Fc refers to the last two constant region immunoglobulin domains of IgA, IgD, and IgG, and the last three constant region immunoglobulin domains of IgE and IgM. In a preferred embodiment, the Fc domain is derived from a human or murine immunoglobulin. In a more preferred embodiment, the Fc domain is derived from human IgG1 or murine IgG2a including the $C_H2$ and $C_H3$ regions.

c. Single Polypeptide Antibodies

In another embodiment, the targeting domains are single polypeptide antibodies that bind to cell surface antigens or receptors that are specifically expressed on tumor cells or are overexpressed on tumor cells as compared to normal tissue.

IV. Gene Therapy

Vectors expressing a transgene under the control of SEQ ID NO:1 can be used in gene therapy. For example, the nucleic acid constructs can be used to treat arterial disease including ischemic lesions and peripheral arterial disease. The vectors can also be used to treat tumors, diabetic retinopathy and rheumatoid arthritis. Nucleic acid delivery involves introduction of "foreign" nucleic acids into a cell which is ultimately in a live animal. Several general strategies for gene therapy have been studied and have been reviewed extensively (Evelyn 13. Kelly, Gene Therapy, (2007) Greenwood Press, Westport Conn.).

One approach includes nucleic acid transfer into primary cells in culture followed by autologous transplantation of the ex vivo transformed cells into the host, either systemically or into a particular organ or tissue. In one embodiment, vectors under the control of SEQ ID NO:1 containing one or more transgenes are transfected into cells that are administered to a subject in need thereof.

Ex vivo methods can include, for example, the steps of harvesting cells from a subject, culturing the cells, transducing them with an expression vector, and maintaining the cells under conditions suitable for expression of a transgene. These methods are known in the art of molecular biology. The transduction step can be accomplished by any standard means used for ex vivo gene therapy, including, for example, calcium phosphate, lipofection, electroporation, viral infection, and biolistic gene transfer. Alternatively, liposomes or polymeric microparticles can be used. Cells that have been successfully transduced then can be selected, for example, for expression of the coding sequence or of a drug resistance gene. The cells then can be lethally irradiated (if desired) and injected or implanted into the subject.

Nucleic acid therapy can be accomplished by direct transfer of a functionally active DNA into mammalian somatic tissue or an organ in vivo. For example, vectors under the control of SEQ ID NO:1 can be administered directly to a tumor or any site selected for treatment.

DNA transfer can be achieved using a number of approaches described below. These systems can be tested for successful expression in vitro by use of a selectable marker (e.g., G418 resistance) to select transfected clones expressing the DNA, followed by detection of the presence of the expression product (after treatment with the inducer in the case of an inducible system) using an antibody to the product in an appropriate immunoassay. Efficiency of the procedure, including DNA uptake, plasmid integration and stability of integrated plasmids, can be improved by linearizing the plasmid DNA using known methods, and co-transfection using high molecular weight mammalian DNA as a "carrier".

Retroviral-mediated human therapy utilizes amphotrophic, replication-deficient retrovirus systems (Temin, H. M., Human Gene Therapy 1:111 (1990); Temin et al., U.S. Pat. No. 4,980,289; Temin et al., U.S. Pat. No. 4,650,764; Temin et al., U.S. Pat. No. 5,124,263; Wills, J. W. U.S. Pat. No. 5,175,099; Miller, A. D., U.S. Pat. No. 4,861,719). Such vectors have been used to introduce functional DNA into human cells or tissues, for example, the adenosine deaminase gene into lymphocytes, the NPT-II gene and the gene for tumor necrosis factor into tumor infiltrating lymphocytes. Retrovirus-mediated gene delivery generally requires target cell proliferation for gene transfer (Miller, D. G. et al., *Mol. Cell. Biol.* 10:4239 (1990). This condition is met by certain of the preferred target cells into which the present DNA molecules are to be introduced, i.e., actively growing tumor cells.

In addition to virus-mediated gene transfer in vivo, physical means well-known in the art can be used for direct transfer of DNA into cells in vitro that are then transplanted into a subject. Exemplary physical means include administration of plasmid DNA and particle-bombardment mediated gene transfer. Furthermore, electroporation, a well-known means to transfer genes into cell in vitro, can be used to transfer DNA molecules to tissues in vivo.

"Carrier mediated gene transfer" can also be used to deliver the vectors to a subject or specific site for treatment. Preferred carriers are targeted liposomes such as immunoliposomes, which can incorporate acylated mAbs into the lipid bilayer. Polycations such as asialoglycoprotein/polylysine may be used, where the conjugate includes a molecule which recognizes the target tissue (e.g., asialoorosomucoid for liver) and a DNA binding compound to bind to the DNA to be transfected. Polylysine is an example of a DNA binding molecule which binds DNA without damaging it. This conjugate is then complexed with plasmid DNA.

Plasmid DNA used for transfection or microinjection may be prepared using methods well-known in the art, for example using the Qiagen® procedure (Qiagen), followed by DNA purification using known methods, such as the methods exemplified herein.

As further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of 0.001 to 10 mg/kg of body weight daily are administered to mammals. Generally, for intravenous injection or infusion, dosage may be lower.

A. Ischemic Lesions

Vectors containing a transgene under the control of SEQ ID NO:1 can be used to treat ischemic lesions. In these vectors the transgene typically encodes one or more angiogenic factors described above. The vectors can be administered directly to a subject in need thereof or the vectors can be introduced into cells obtained from the subject to be treated or from an allogenic or syngeneic subject. The transfected cells can then be returned to the subject. Once in the subject, the vector will be expressed only in tissue or cells that are able to trigger SEQ ID NO:1. In one embodiment SEQ ID NO:1 is triggered in angiogenic tissue and no detectable activity of the vector is found in other tissue. Preferred tissue or cells in which the vector is active is angiogenic arterial blood vessels, remodeling feeding arteries, growing collateral arteries, arteries undergoing arteriogenesis, human iliac arterial endothelial cells, and smooth muscle cells. The collateral growth or collateralization occurs in or upstream of ischemic tissues through the process called arteriogenesis. When an artery senses persistent blood flow increase, caused by high oxygen and nutrients demands from ischemic tissue, the artery responds by remodeling its wall to increase its diameter and accommodate high blood flow. SEQ ID NO:1 induces transgene expression in any artery undergoing this type of remodeling. Once activated the vector expresses an effective amount of the angiogenic factor to promote formation and/or growth of blood vessels. Typically, the angiogenic factor is secreted to the extracellular environment where it acts to promote angiogenesis.

The ischemic lesion to be treated can be in any tissue or organ. Preferred ischemic lesions to be treated are found in cardiac tissue, leg, central nervous system, and eye.

B. Tumors

Vectors encoding a transgene under the control of SEQ ID NO:1 can also be used to treat tumors. Vectors used to treat tumors have transgenes that encode a cytotoxin or a pro-apoptotic polypeptide described above. When administered to a subject locally at and around a site of a tumor, or locally in the tumor feeding arteries, the vector is expressed in vascular tissue supplying the tumor with blood. Expression of the cytotoxin or pro-apoptotic polypeptide causes the death of the angiogenic tissue cells. Tumor cells are also killed as the cytotoxin or pro-apoptotic polypeptide is released or secreted from the angiogenic tissue. Expression of an anti-angiogenic polypeptide causes reduction in new vessel formation in tumors and inhibits its growth.

The vectors provided herein are useful for treating cancer by administering to subject an amount of the vector effective to treated cancer of the organs including but not limited to: bladder, brain, breast, cervical, colo-rectal, esophageal, kidney, liver, nasopharangeal, pancreatic, prostate, skin, stomach, uterine, ovarian, and testicular.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

C. Angiogenic Arthritic or Diabetic Tissues

Vectors encoding a transgene under the control of SEQ ID NO:1 can also be used to treat diabetic retinopathy, rheumatoid arthritis, and peripheral artery disease. Vectors used to treat angiogenic arthritic tissues, such as those in rheumatoid arthritis, may have transgenes that encode anti-inflammatory peptides or polypeptides. Exemplary ant-inflammatory peptides and polypeptides include, but are not limited to, IL-6 receptor, IL-1 R antagonist homolog 1, IL-10 R beta, IL-10 R alpha, TNF Receptor member 1B, TNF receptor member 5, TNF receptor member 11b, IK cytokine down-regulator of HLA H, TGF-B inducible early growth response 2, CD2, IL-19, IL-10, and the antiflammain (AFs) which correspond to uteroglobin residues 39-47 and lipocortin residues 246-254. Vectors used to treat diabetic tissues, such as those that develop in diabetic retinopathy and peripheral artery disease, may have transgenes that encode an angiogenic polypeptide described above, including the ones that induce vascular wall maturation.

In diabetic retinopathy, new vessels are needed. These vessels are, however, very immature and leaky, which often leads to hemorrhage and blindness. In one embodiment these vessels are matured by recruiting smooth muscle cells (SMCs) and promoting extracellular matrix (ECM) production. Vectors for treating diabetic retinopathy include a transgene under control of SEQ ID NO:1 encoding growth factors such as platelet-derived growth factor (PDGF), which recruits SMCs, and/or angiopoietin 1, which stabilizes endothelial interaction with ECM.

When administered to a subject systemically or locally at a site of an angiogenic arthritic or diabetic tissues, the vector is expressed in angiogenic tissue supplying the diabetic or arthritic with blood. Expression of the anti-inflammatory and angiogenic polypeptide cause decrease in joint inflammation in arthritic tissues and production of stable vasculatures in diabetic tissues, respectively.

V. Transgenic Hosts

Non-human transgenic organisms containing SEQ ID NO:1 are also provided. The non-human transgenic organisms include primates, mice, rats, guinea pigs, rabbits, pigs, and horses. Cells containing SEQ ID NO:1 include eukaryotic and prokaryotic cells. Methods of making transgenic organisms and transfected cells are routine in the art.

VI. Pharmaceutical Compositions

The vectors having one or more transgenes under control of SEQ ID NO:1 are preferably employed for therapeutic uses in combination with a suitable pharmaceutical carrier. Such compositions comprise an effective amount of the vector, and a pharmaceutically acceptable carrier or excipient. The formulation is made to suit the mode of administration.

Pharmaceutically acceptable carriers are determined in part by the particular composition being administered, as well as by the particular method used to administer the composition. Accordingly, there is a wide variety of suitable formulations of pharmaceutical compositions containing the nucleic acids.

It is understood by one of ordinary skill in the art that nucleotides administered in vivo are taken up and distributed to cells and tissues (Huang, et al., *FEBS Lett.* 558(1-3):69-73 (2004)). For example, Nyce et al. have shown that antisense oligodeoxynucleotides (ODNs) when inhaled bind to endogenous surfactant (a lipid produced by lung cells) and are taken up by lung cells without a need for additional carrier lipids (Nyce and Metzger, *Nature*, 385:721-725 (1997). Small nucleic acids are readily taken up into T24 bladder carcinoma tissue culture cells (Ma, et al., *Antisense Nucleic Acid Drug Dev.* 8:415-426 (1998).

The compounds may be in a formulation for administration topically, locally or systemically in a suitable pharmaceutical carrier. Remington's Pharmaceutical Sciences, 15th Edition by E. W. Martin (Mark Publishing Company, 1975), discloses typical carriers and methods of preparation. The compound may also be encapsulated in suitable biocompatible microcapsules, microparticles or microspheres formed of biodegradable or non-biodegradable polymers or proteins or liposomes for targeting to cells. Such systems are well known to those skilled in the art and may be optimized for use with the appropriate nucleic acid.

Various methods for nucleic acid delivery are described, for example, in Sambrook et al., 1989, *Molecular Cloning: A Laboratory Manual*, Cold Spring Harbor Laboratory, New York; and Ausubel et al., 1994, *Current Protocols in Molecular Biology*, John Wiley & Sons, New York. Such nucleic acid delivery systems comprise the desired nucleic acid, by way of example and not by limitation, in either "naked" form as a "naked" nucleic acid, or formulated in a vehicle suitable for delivery, such as in a complex with a cationic molecule or a liposome forming lipid, or as a component of a vector, or a component of a pharmaceutical composition. The nucleic acid delivery system can be provided to the cell either directly, such as by contacting it with the cell, or indirectly, such as through the action of any biological process. The nucleic acid delivery system can be provided to the cell by endocytosis, receptor targeting, coupling with native or synthetic cell membrane fragments, physical means such as electroporation, combining the nucleic acid delivery system with a polymeric carrier such as a controlled release film or nanoparticle or microparticle, using a vector, injecting the nucleic acid delivery system into a tissue or fluid surrounding the cell, simple diffusion of the nucleic acid delivery system across the cell membrane, or by any active or passive transport mechanism across the cell membrane. Additionally, the nucleic acid delivery system can be provided to the cell using techniques such as antibody-related targeting and antibody-mediated immobilization of a viral vector.

Formulations for topical administration may include ointments, lotions, creams, gels, drops, suppositories, sprays, liquids and powders. Conventional pharmaceutical carriers, aqueous, powder or oily bases, or thickeners can be used as desired.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions, solutions or emulsions that can include suspending agents, solubilizers, thickening agents, dispersing agents, stabilizers, and preservatives. Formulations for injection may be presented in unit dosage form, e.g., in ampules or in multi-dose containers, with an added preservative. The compositions may take such forms as sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, injectable organic esters such as ethyl oleate, or fixed oils including synthetic mono or di-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, and electrolyte replenishers (such as those based on Ringer's dextrose). Preservatives and other additives may also be present such as, for example, antimicrobials, antioxidants, chelating agents and inert gases. In addition, sterile, fixed oils are conventionally employed as a solvent or suspending medium. For this purpose any bland fixed oil including synthetic mono- or diglycerides may be employed. In addition, fatty acids such as oleic acid may be used in the preparation of injectables. Carrier formulation can be found in Remington's Pharmaceutical Sciences, Mack Publishing Co., Easton, Pa. Those of skill in the art can readily determine the various parameters for preparing and formulating the compositions without resort to undue experimentation.

The compound alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and air. For administration by inhalation, the compounds are delivered in the form of an aerosol spray presentation from pressurized packs or a nebulizer, with the use of a suitable propellant.

In some embodiments, the compound described above may include pharmaceutically acceptable carriers with formulation ingredients such as salts, carriers, buffering agents, emulsifiers, diluents, excipients, chelating agents, fillers, drying agents, antioxidants, antimicrobials, preservatives, binding agents, bulking agents, silicas, solubilizers, or stabilizers. In one embodiment, the compounds are conjugated to lipophilic groups like cholesterol and laurie and lithocholic acid derivatives with C32 functionality to improve cellular uptake. For example, cholesterol has been demonstrated to enhance uptake and serum stability of nucleic acids in vitro (Lorenz, et al., *Bioorg. Med. Chem. Lett.* 14(19):4975-4977 (2004)) and in vivo (Soutschek, et al., *Nature* 432(7014):173-178 (2004)). In addition, it has been shown that binding of steroid conjugated oligonucleotides to different lipoproteins in the bloodstream, such as LDL, protect integrity and facilitate biodistribution (Rump, et al., *Biochem. Pharmacol.* 59(11):1407-1416 (2000)). Other groups that can be attached or conjugated to the compound described above to increase cellular uptake, include acridine derivatives; cross-linkers such as psoralen derivatives, azidophenacyl, proflavin, and azidoproflavin; artificial endonucleases; metal complexes such as EDTA-Fe (II) and porphyrin-Fe(II); alkylating moieties; nucleases such as alkaline phosphatase; terminal transferases; abzymes; cholesteryl moieties; lipophilic carriers; peptide conjugates; long chain alcohols; phosphate esters; radioactive markers; non-radioactive markers; carbohydrates; and polylysine or other polyamines. U.S. Pat. No. 6,919,208 to Levy, et al., also describes methods for enhanced delivery. These pharmaceutical formulations may be manufactured in a manner that is itself known, e.g., by means of conventional mixing, dissolving, granulating, levigating, emulsifying, encapsulating, entrapping or lyophilizing processes.

EXAMPLES

Example 1

Tg(Alk1PIB-lacZ) Transgenic Mice

Methods and Materials
ECR Analyses and Tg(Alk1PIB-lacZ) Mouse Generation
Alignments of the mouse Alk1 gene and regulatory fragments to human genomic sequences were obtained from the ECR Browser (Ovcharenko, I., et al., *Nucleic Acids Res;* 32:W280-286 (2004))(http://ecrbrowser.dcode.org) by searching with the ALK1 gene symbol "ACVRL1." The ECR Browser displays pre-computed alignments of publicly available genome sequences and highlights ECRs.

Based on the ECR analysis, the following conserved DNA fragments were isolated from mouse Alk1 genomic DNA: the promoter region (Prom), which is a 2.6 kb EcoRI-EcoRI fragment covering 1.7 kb of the promoter, exon 1, intron 1, exon 2, and a part of intron 2, as well as the 3' region of intron 2 (Int2B), which is a 2.2 kb BglII-BglII fragment covering 2 kb of intron 2 and a part of exon 3 (0.2 kb) upstream of the translation start site. The Prom and Int2B fragments were ligated to create the 4.8 kb Alk1 PIB regulatory fragment. The Alk1PIB-lacZ construct was created by subcloning the Alk1PIB fragment upstream of the pSIB reporter cassette28, which contains the Simian virus 40 (SV40) splice donor/acceptor sites (SD/SA), internal ribosome entry site (IRES), and the lacZ reporter gene (FIG. 1).

Microinjection of the above construct into male pronuclei of fertilized eggs from the C57BL/6 strain was performed at the transgenic animal core facilities at the Medical College of Georgia and at the University of Florida. Founder lines were screened by genomic Southern blot using the lacZ gene as a probe. Ten founder lines were further examined for transgene expression by X-gal staining of organs at various ages. Consequently, three new mouse lines, TgA8, E16, and F8, were established. The transgene-positive animals were identified by X-gal staining of tail tips at two to three weeks old and/or by polymerase chain reaction (PCR) of tail genomic DNA using forward primer in Alk1 intron 2 sequence, agtgaaccaggacttcccttgcag (SEQ ID NO:2) and reverse primer in SD/SA sequence, cgggtacaattccgcagcttttag (SEQ ID NO:3).

Results
Evolutionary conserved regions (ECRs) in intergenic and intron sequences are most likely to have functional importance, especially in the regulation of gene expression (Ovcharenko, I., et al., *Nucleic Acids Res,* 32:W280-286 (2004)). A shortened regulatory fragment, Alk1PIB, of the 9.2 kb pXh4.5-in2 Alk1 regulatory fragment was created by eliminating non-conserved sequences and connecting the conserved promoter (Prom) and the 3' half of intron 2 (Int2B). The 4.8 kb Alk1 FIB fragment was ligated to a lacZ reporter cassette to generate a transgenic construct, Alk1PIB-lacZ (FIG. 1), and three transgenic mouse lines, Tg(Alk1PIB-lacZ) A8, R16, and F8, (TgA8, TgE16, TgF8 hereafter) were established.

The targeting ability of the Alk1 PIB fragment was visualized by X-gal staining. Upon application of X-gal staining solution, the lacZ gene product, β-galactosidase, hydrolyzes X-gal to produce an insoluble blue dye. Hence, blue staining in cells indicates active transcription from the Alk1PIB regulatory fragment Analyses of the three transgenic mouse lines showed that the Alk1PIB activities during the postnatal stages were largely consistent among the three lines, with some ectopic expression found only in the TgA8 line. This ectopic expression was observed in cerebellar Perkinje neurons (strong expression), a small number of skeletal muscle fibers (moderate expression), cardiac muscle cells (weak expression), and some other organs (very weak expression). Overall, TgA8 line had the strongest staining intensities among the three lines. Unless otherwise indicated, expression patterns commonly observed in all three lines are described below.

Example 2

Immunohistochemical Analysis of Tg(Alk1PIB-lacZ) Transgenic Mice

Methods and Materials

X-Gal Staining, Clearing, Histology, and Immunohistochemistry

The following mouse organs were examined for transgene expression at birth (newborn), at two to three weeks, and at 12-16 weeks (adult): brain, heart, lungs, liver, mesenteric membrane, abdominal skeletal muscles, skin, and aorta. In addition, the kidneys, adrenal glands, ovary, and uterus from adult mice were examined. Tissue sample preparation, X-gal staining, and immunohistochemistry were performed as previously described (Seki, T., et al., Circ Res, 93:6852-689 (2003)). Briefly, tissue samples were dissected in 1-2 mm slices to facilitate penetration of the X-gal solution and were stained overnight. The stained samples were then photographed and fixed with 10% formalin, 4% paraformaldehyde, or zinc fixative, followed by embedding in paraffin for histology or cleared with 1:1 mixture of benzyl alcohol and benzyl benzoate (both from Sigma-Aldrich, St. Louis, Mo.) for whole mount imaging. Once cleared, the tissues become transparent, and blue staining at any depth could be observed. Following a published protocol (Nagy, A., et al., In: Inglis 3, Cuddihy J (eds). Manipulation the Mouse Embryo: A Laboratory Manual, 3rd Edition edn. Cold Spring Harbor Laboratory Press: Cold Spring Harbor, N.Y., 2003, pp 687-691), some of the tissues were embedded in OCT compound, frozen-sectioned, and then X-gal stained for observation as well. Anti-platelet/endothelial cell adhesion molecule 1 (PECAM, clone: Mec13.3; BD Biosciences, San. Jose, Calif.) and anti-smooth muscle α-actin (SMA, clone: 1A4; Sigma-Aldrich) antibodies were used to identify endothelial and smooth muscle cells, respectively. Tissues from littermate wild-type C57 mice were used as a negative control.

Results

The overall regulatory activities of the Alk1PIB fragment during postnatal growth stages and in adults were blood vessel-specific and similar to that seen for the endogenous Alk1 gene. The transgene showed high expression in the lungs throughout postnatal life and no expression in the liver. In other organs, expression was evident in the arteries and some capillaries during postnatal growth stages and then diminished at the adult stage, which are comparable to the endogenous Alk1 expression pattern observed in $Alk1^{+/lacZ}$ and Tg(Alk1-lacZ) mice.

Histological analysis indicated that expression of the transgene in young animals was localized in vascular ECs and smooth muscle cells (SMCs) in all of the organs examined. Faint expression was observed in some venous ECs and SMCs, but most was observed in arterial and capillary ECs, which was consistent with expression of endogenous Alk1. Although endogenous Alk1 was seldom detected in SMCs, the Alk1PIB fragment was active in some vascular SMCs. Both positive and negative SMCs were found in random order in a section of an artery. In adults, transgene expression was virtually diminished in all organs except the lungs. A more thorough investigation identified a small number of positively stained arteries in various organs, most often in the brain, and that staining was localized in arterial ECs and SMCs.

Example 3

Alk1PIB Targeting Activity in Angiogenic Lesions and Wound Healing

Methods and Materials

Wound Healing and Subcutaneous Tumor Models

The wound healing model was created by placing three 4-mm-diameter full-thickness excisional wounds on the mid-dorsum using a biopsy punch as previously described (Seld, T., et al., Circ Res, 93:6852-689 (2003)). All three mouse lines were tested. The wounds were left unsutured, and the areas had completely recovered after 14 days in most cases. The mice were euthanized on days 3, 5, 8, 10, and 14 after wounding, and the skins were processed for X-gal staining and photography.

Mouse B16-F10 melanoma cells were purchased from the American Type Cell Culture (ATCC, Manassas, Va.) and propagated as recommended. One million cells were injected subcutaneously into 8 to 12 week old TgA8 mice. Tumor size was measured as ½×length×width (length>width). Only a few tiny tumors were palpable at the injection sites seven days after injection (day 7). The tumor and surrounding skin samples were prepared on days 14, 21, and 28 (n=3 each). At each time point, mice harboring relatively large tumors were selected from the remaining animals to analyze for active angiogenesis in the lesions. The samples were processed for X-gal staining and photographed.

Results

During wound healing, the Alk1 P18 fragment transiently induced transgene expression in the arteries feeding wound lesions. Full thickness sldn wounds were created on mouse skin, and the skin samples were collected at several time points for each of the mouse lines. As in Alk1+lacZ mice, transient expression was detected in blood vessels from the samples on day 5 (TgA8; days 8 and 10 (TgE16); and days 3, 5, and 8 (TgFS). The staining diminished once wounds were completely healed. Expression was limited to arteries, where expression was seen in both arterial ECs and SMCs.

To observe Alk1PIB activity in another angiogenic model, mouse B16 melanoma cells were injected into TgA8 mice to create subcutaneous tumors. Endogenous Alk1 has been shown to be activated in newly forming and feeding arteries in a teratoma model (Seki, T., et al., Circ Res, 93:6852-689 (2003)). In. TgA8 mice, subcutaneous B 16 tumors were rarely palpable on day 7 (n=3; 0-1.5 mm3). On day 14, many of the injection sites had detectable tumors (n=3; 64-648 mm3); however, Alk1PIB activity was detected only in a few feeding arteries, even in the mouse with the largest tumor at this stage. As tumor sizes increased on days 21 (n=3; 543-955 mm3) and 28 (n=3; 939-2475 mm3), Alk1PIB was clearly active in the feeding arteries of these larger tumors. Histological sections of 816 tumors revealed X-gal stained arteries in connective tissues encapsulating tumors, but none were identified inside the tumors.

Example 4

Vectors Having Alk1PIB Regulatory Activity

Methods and Materials

Recombinant Adenovirus Production

Promoter fragments of the CMV, the human VEGF-R1 (hFLT1) gene (Nicklin, S. A., et al., Hypertension, 38:65-70 (2001)), and the hICAM2 gene (Cowan, P. J., et al., Transplantation, 62:155-160 (1996); Cowan, P. J., et al., Xenotransplantation, 10:223-231 (2003)), as well as the Alk1PIB fragment were first individually subcloned into pENTR vectors (Invitrogen, Carlsbad, Calif.), followed by addition of a ZsGreen1-DR (ZsG) green fluorescent protein gene excised from pZsGreen1-DR vector (Clontech Laboratories, Inc., Mountain View, Calif.). The CMV-ZsG, hFLT1-ZsG, hICAM2-ZsG, and ALK1PIB-ZsG sequences in the pENTR vector were transferred to the destination vector pAd/

PL-DEST (Invitrogen), with the Gateway Clonase II Enzyme Mix (Invitrogen) to create pAd-CMV-ZsG, pAd-hFLT1-ZsG, pAd-hICAM2-ZsG, and pAd-Alk1PIB-ZsG constructs, respectively. They were then transfected into 293A cells (Invitrogen) using ProFection Mammalian Transfection Systems (Promega, Madison, Wis.), and virus particles were produced. A large-scale amplification, cesium chloride (CsCl) purification, and titration of the viruses were performed by Vector Biolabs, Inc. (Philadelphia, Pa.).

Promoter Activity Assay in HIAECs and Fibroblasts

Primary HIAECs (Lonza Walkersville, Inc., Walkersville, Md.) were propagated according to the manufacturer's recommendation. Telomerase induced immortalized fibroblasts (Bodnar, A. G., *Science,* 279:349-352 (1998)) were propagated in Dulbecco's modified Eagle's medium (DMEM) supplemented with 10% fetal calf serum. For adenovirus infection, HIAECs at passage five and fibroblasts were trypsinized and plated into 24-well plates at $5\times10^4$ cells/well density, and the cells were infected with $5\times10^7$ plaque forming unit (pfu) recombinant adenoviruses on the following day. A media change was performed 16 hours after infection. The cells were then incubated in complete media for four days, and a medium change was performed every two days. The numbers of the ZsG expressing cells were counted as follows: three fluorescence images and their corresponding phase contrast images, one from the center and two from the peripheral of the well, were taken from each well using fluorescence microscopy with 10× objective lens and 101 ms exposure time, and the numbers of the cells in the images were then counted. Because Ad-CMV-ZsG virus expressed ZsG protein very intensely, three ms exposure images were used for counting instead.

Results

Figure 2:
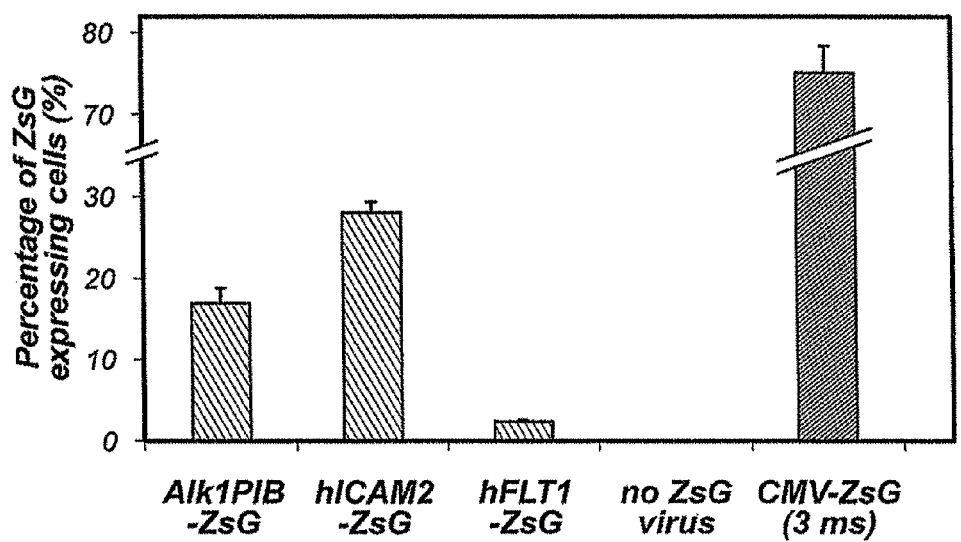
FIG. 2 is a bar graph showing the percentage of ZsG fluorescent cells that was positive after recombinant adenoviruses infection with Ad-Alk1PIB-ZsG. Note that the 3 ms exposure images were used for counting Ad-CMV-ZsG infected cells, and the proportion is not directly comparable to the other viruses. Data represent mean plus or minus SE of three replicates.

Even with 312 ms exposure, ZsG expression was not found in the fibroblasts infected with Ad-Alk1PIB-ZsG, Ad-hICAM2-ZsG, and Ad-hFLT1-ZsG viruses. On average, a total of 1333±SD 115.2 HIAECs (n=12 wells) were found in the three images taken from a single well. Each virus was infected to three independent wells, and the average number of positive cells and standard error were calculated. The infection was repeated at least three times, and a representative data are shown in FIG. 2.

Recombinant adenoviruses carrying a reporter transgene, ZsGreen1-DR green fluorescent protein (ZsG), were generated with four regulatory fragments, including Alk1PIB, human ICAM2 (hICAM2), human VEGF-R1 (fms-like tyrosine kinase 1, hFLT1), and cytomegalovirus early promoter (CMV). The viruses were used to infect human arterial endothelial cells (HIAECs) (FIG. 2) and fibroblasts. No detectable ZsG expression was observed in fibroblasts with Ad-Alk1PIB-ZsG, Ad-hICAM2-ZsG, or Ad-hFLT1-ZsG viruses, illustrating their EC specificity. Ad-CMV-ZsG virus induced ZsG expression in most of the HIAECs; however, the expression levels varied from cell to cell, suggesting infection heterogeneity. To quantify the transgene expression, the number of ZsG expressing cells and total number of cells in the digital images were counted to determine the proportion of ZsG expressing cells. The Alk-1PIB induced ZsG expression in 17.0±1.9% of HAECs, which was higher than hFLT1 (2.3±0.3%) and lower than hICAM2 (28.2±1.2%) (FIG. 2). These results indicate that the Alk1 PIB fragment can be utilized in an adenovirus vector.

I claim:

1. A vector comprising SEQ ID NO:1.

2. The vector of claim 1 wherein the vector is an expression vector.

3. The vector of claim 1 further comprising a nucleotide sequence encoding a polypeptide.

4. The vector of claim 3 wherein the polypeptide induces apoptosis.

5. The vector of claim 3 wherein the polypeptide is selected from the group consisting of p53, p16, p21, p27, an E2F transcription factor, fragile histidine triad (FHIT), phosphatase and tensin homolog (PTEN), and caspase 1-10.

6. The vector of claim 3, wherein the nucleotide sequence encoding a polypeptide is under control of SEQ ID NO:1.

7. An expression vector comprising a promoter operably linked to a transgene under control of SEQ ID NO:1.

8. The expression vector of claim 7 wherein the vector is an adenovirus vector.

* * * * *